US009145428B2

(12) United States Patent
Emonds et al.

(10) Patent No.: US 9,145,428 B2
(45) Date of Patent: *Sep. 29, 2015

(54) METHODS AND SYSTEMS FOR FORMING BORONIC ACIDS AND INTERMEDIATES THEREOF

(75) Inventors: Mark V. M. Emonds, Midland, MI (US); Catherine A. Menning, Midland, MI (US); D. Wayne Blaylock, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 201 days.

This patent is subject to a terminal disclaimer.

(21) Appl. No.: 13/618,128

(22) Filed: Sep. 14, 2012

(65) Prior Publication Data

US 2013/0066115 A1 Mar. 14, 2013

Related U.S. Application Data

(60) Provisional application No. 61/534,768, filed on Sep. 14, 2011.

(51) Int. Cl.
  *C07F 5/04* (2006.01)
  *C07F 5/02* (2006.01)
  *B01J 19/00* (2006.01)
  *B01J 19/24* (2006.01)

(52) U.S. Cl.
  CPC ............. *C07F 5/025* (2013.01); *B01J 19/0093* (2013.01); *B01J 19/24* (2013.01); *B01J 2219/0004* (2013.01); *B01J 2219/00011* (2013.01); *B01J 2219/0086* (2013.01); *B01J 2219/00094* (2013.01); *B01J 2219/00099* (2013.01); *B01J 2219/00795* (2013.01); *B01J 2219/00813* (2013.01); *B01J 2219/00822* (2013.01); *B01J 2219/00867* (2013.01); *B01J 2219/00873* (2013.01); *B01J 2219/00894* (2013.01)

(58) Field of Classification Search
  USPC .......................................... 568/1, 6; 570/124
  See application file for complete search history.

(56) References Cited

U.S. PATENT DOCUMENTS

| 7,300,907 B2 | 11/2007 | Epp et al. |
| 7,314,849 B2 | 1/2008 | Balko et al. |
| 7,611,647 B2 * | 11/2009 | Arndt et al. ............... 260/665 R |
| 2002/0161230 A1 | 10/2002 | Meudt et al. |
| 2007/0015931 A1 | 1/2007 | Terranova et al. |
| 2010/0121058 A1 | 5/2010 | Guenthenspberger et al. |

FOREIGN PATENT DOCUMENTS

WO WO2007017432 2/2007

OTHER PUBLICATIONS

International Search Report and Written Opinion for PCT/US2012/055605, dated Feb. 5, 2013.
Gross, Timothy et al., "Chemical development of NBI-75043. Use of a flow reactor to circumvent a batch-limited metal-halogen exchange reaction," Organic Process Research & Development, 2008, pp. 929-939, vol. 12, No. 5.
Hessel, V. et al., "Selectivity gains and energy savings for the industrial phenyl boronic acid process using micromixer/tubular reactors," Organic Process Research & Development, 2004, pp. 511-523, vol. 8, No. 3.

* cited by examiner

*Primary Examiner* — Sudhakar Katakam
*Assistant Examiner* — Pancham Bakshi
(74) *Attorney, Agent, or Firm* — Michael R. Asam; TraskBritt, P.C.

(57) ABSTRACT

Methods for forming boronic acids, and intermediates thereof, are disclosed. The method may include mixing a 1-chloro-2-substituted-3-fluorobenzene starting material with an alkyllithium in a first reactor to form a reaction mixture. The 1-chloro-2-substituted-3-fluorobenzene starting material may react with the alkyllithium to form a lithiated intermediate. The reaction mixture may be continuously transferred to a second reactor and a borate may be continuously introduced to form a boronate. The boronic acids may be formed by treating the boronate with aqueous potassium hydroxide followed by acidification. Such methods may provide continuous formation of the boronic acids and may reduce an amount of a reactive intermediate present during processing as well as cycle times. Systems for forming the boronic acids are also disclosed.

25 Claims, 5 Drawing Sheets

METHODS AND SYSTEMS FOR FORMING BORONIC ACIDS AND INTERMEDIATES THEREOF

CROSS-REFERENCE TO RELATED APPLICATION

This application claims the benefit of U.S. Provisional Patent Application Ser. No. 61/534,768, filed Sep. 14, 2011, the disclosure of which is hereby incorporated herein in its entirety by this reference.

TECHNICAL FIELD

Various aspects and embodiments relate generally to methods of forming boronic acids, intermediate compounds thereof and systems for performing the same.

BACKGROUND

U.S. Pat. Nos. 7,314,849 and 7,300,907 describe respectively certain 6-(poly-substituted aryl)-4-aminopicolinate and 2-(poly-substituted aryl)-6-amino-4-pyrimidinecarboxylic acid compounds and their use as herbicides. 2-Fluoro-3-substituted-4-chlorophenylboronic acid and derivatives thereof are useful intermediates for the preparation of these herbicides.

For example, 2-fluoro-3-substituted-4-chlorophenylboronic acid derivatives may be prepared by halogen-metal exchange of 1-bromo-2-fluoro-3-substituted-4-chlorobenzenes with n-butyllithium followed by quenching with a boronic acid ester. As described in U.S. Pat. No. 7,611,647 to Arndt et al., 1-chloro-2-substituted-3-fluorobenzenes may be selectively deprotonated and functionalized in a position adjacent to the fluoro substituent. Selective deprotonation in the position adjacent to the fluoro substituent is achieved by contacting the 1-chloro-2-substituted-3-fluorobenzene starting material with an alkyl lithium compound under anhydrous conditions in an inert organic solvent.

Current methods used to synthesize 4-chloro-2-fluoro-3-methoxyphenylboronic acid (PBA) and derivatives thereof require that the 2-chloro-6-fluoroanisole (2,6-CFA) precursor be cooled to less than about −28° C., and less than about −50° C. in particular embodiments, and treated with butyllithium to form a lithio-2,6-CFA (Li-2,6-CFA) intermediate. This intermediate compound must be kept at a temperature of less than about −50° C. to prevent decomposition, and less than about −28° C. to prevent rapid decomposition, eliminating lithium fluoride to form reactive benzyne species. Producing PBA on a large scale in a batch process, thus, requires cooling of a large volume of solution and the accumulation of a large amount of the reactive intermediate Li-2,6-CFA.

BRIEF SUMMARY

Embodiments of the present disclosure include methods of forming boronic acids, such as 4-chloro-2-fluoro-3-methoxyphenylboronic acid (PBA) and derivatives thereof. The methods may include reacting a 1-chloro-2-substituted-3-fluorobenzene with at least one alkyllithium to form a reaction mixture comprising a lithiated intermediate, continuously adding a borate to the reaction mixture to form a boronate, and converting the boronate to the boronic acid.

In further embodiments the methods may include continuously forming a lithiated intermediate by reacting a 1-chloro-2-substituted-3-fluorobenzene with at least one alkyllithium, reacting the lithiated intermediate with a borate to form a boronate, and converting the boronate to the boronic acid.

Embodiments of the present disclosure further include methods of forming intermediate compounds. The methods may include reacting a 1-chloro-2-substituted-3-fluorobenzene with at least one alkyllithium to form a reaction mixture comprising a lithiated intermediate in a first reactor, transferring the reaction mixture to a second reactor, and adding a borate to the reaction mixture in the second reactor to form a boronate.

In yet further embodiments, the present disclosure includes systems for forming a boronic acid. The systems include a first reactor flowably interconnected to a 1-chloro-2-substituted-3-fluorobenzene source and an alkyllithium source, a second reactor flowably interconnected to a borate source, and a transfer tube configured for transferring a liquid from the first reactor to the second reactor.

The foregoing and other features will become more apparent from the following detailed description of several embodiments, which proceeds with reference to the accompanying figures.

DETAILED DESCRIPTION

Figure 1:
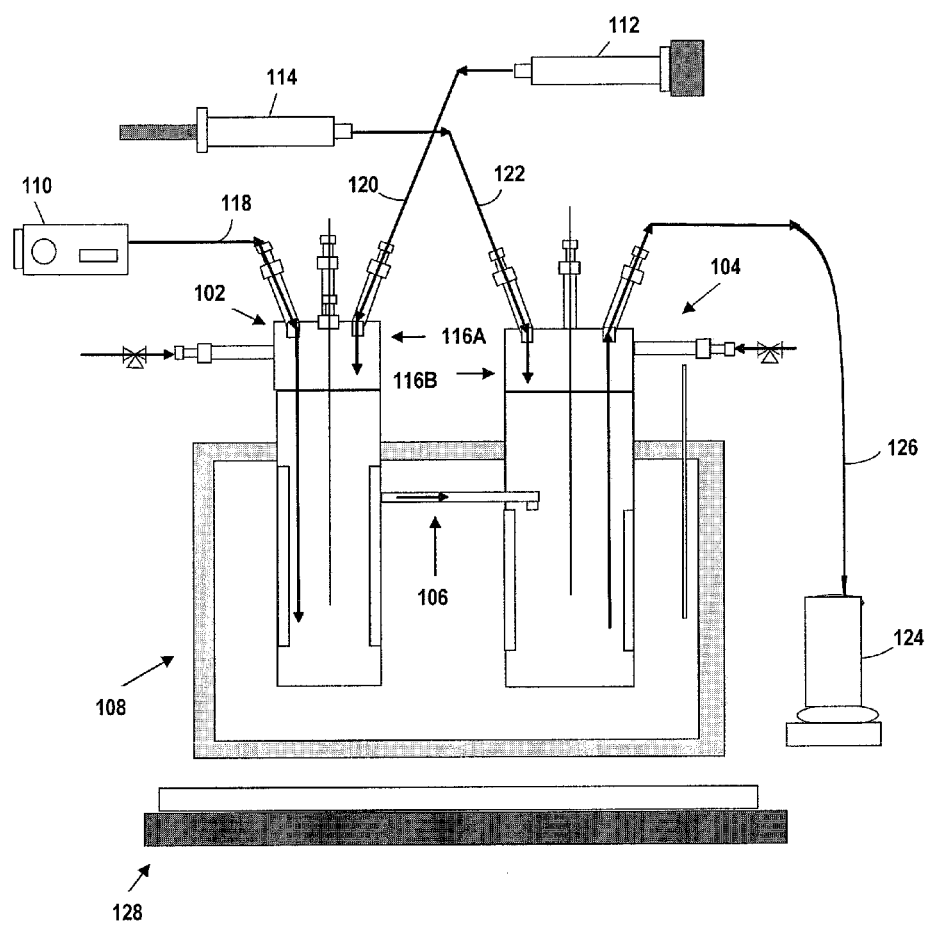
FIG. 1 is a schematic diagram of an embodiment of a system used to form boronic acids using continuous stirred-tank reactors.

As used herein, the term "alkyllithium" refers to a compound including lithium and an alkyl group, such as, methyl, ethyl, propyl, butyl or hexyl. For example, the alkyllithium may be a butyllithium, such as n-butyllithium, t-butyllithium or sec-butyllithium.

Embodiments of methods for forming boronic acids, such as 4-chloro-2-fluoro-3-methoxyphenylboronic acid (PBA) and derivatives thereof, are disclosed. Such methods provide continuous formation of the boronic acids that minimize an amount of a reactive intermediate at any given time and provide reduced cycle times in comparison to conventional methods. The boronic acid may include, for example, 4-chloro-2-fluoro-3-methoxyphenylboronic acid. A 1-chloro-2-substituted-3-fluorobenzene starting material may be mixed with an alkyllithium in a first reactor to form a reaction mixture. In the reaction mixture, the 1-chloro-2-substituted-3-fluorobenzene may react with the alkyllithium to form a lithiated intermediate. The lithiated intermediate may be a reactiver species that is susceptible to decomposition by elimination of lithium fluoride, resulting in the undesirable formation of a highly reactive, substituted benzyne. For example, the lithiated intermediate may decompose at temperatures of greater than about −50° C., and may decompose rapidly at temperatures of greater than about −28° C. The reaction mixture may be continuously transferred to a second reactor and a borate may then be continuously introduced to the second reactor. In the second reactor, the lithiated intermediate may be continuously reacted with the borate to form the boronate before decomposition of the lithiated intermediate occurs. The boronate may be converted to a boronic acid by treatment with aqueous potassium hydroxide (KOH) followed by acidification, as will be described in further detail.

In some embodiments, a 2-chloro-6-fluoroanisole (2,6-CFA) starting material is reacted with n-butyllithium in solution to form a reaction mixture including 6-chloro-2-fluoro-3-litihioanisole (Li-2,6-CFA). Trimethyl borate may significant decomposition. Operation at higher temperatures would further improve energy efficiency, and reduce equipment size, equipment costs, and overall cycle time.

As shown in the reaction scheme below, during formation of PBA, the lithiated intermediate (Li-2,6-CFA) is maintained at temperatures of less than −40° C. and, in particular embodiments, less than −60° C. to provide a safety margin and to prevent undesirable side reactions. For example, as the lithiated intermediate is exposed to temperatures of greater than −60° C., elimination of lithium fluoride from the lithiated intermediate may result in formation of a highly reactive, substituted benzyne. At temperatures of greater than about −28° C., this decomposition becomes much more rapid.

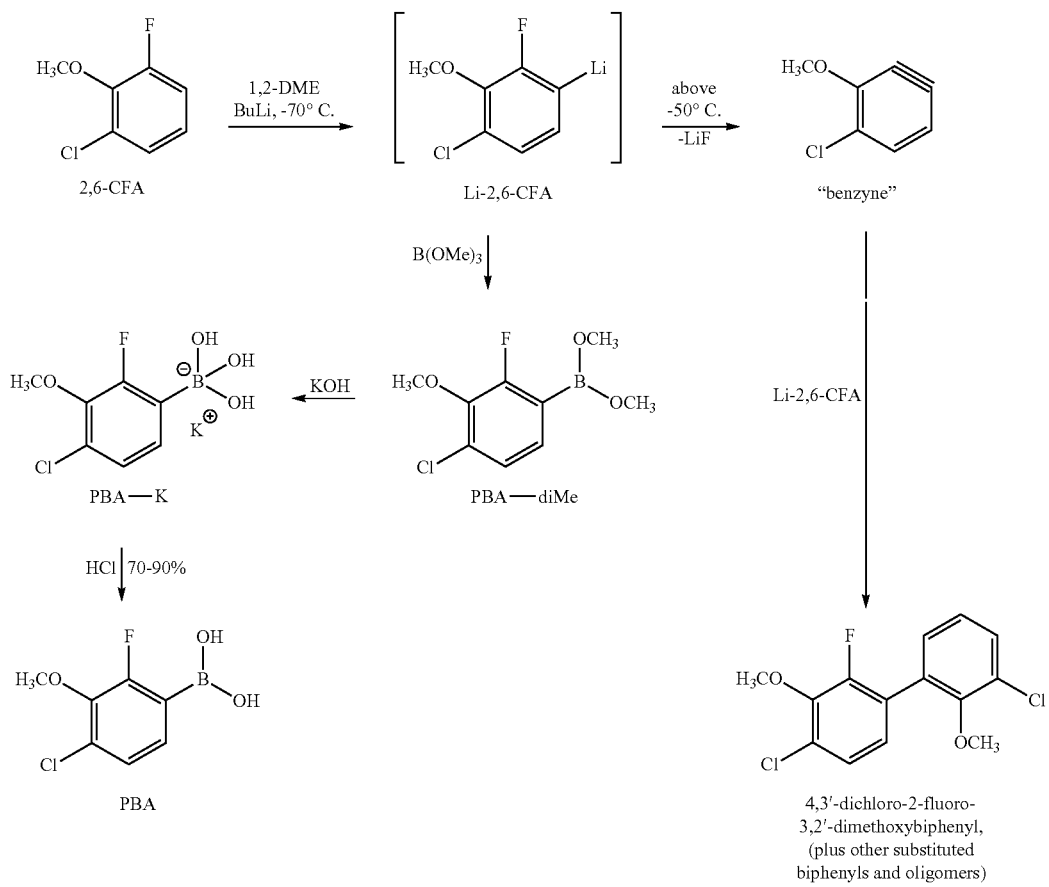

be continuously introduced to the reaction mixture where it may react with the Li-2,6,CFA to form 4-chloro-2-fluoro-3-methoxyphenylboronate (PBA-diMe). The PBA-diMe may then be converted to 4-chloro-2-fluoro-3-methoxyphenylboronic acid (PBA).

Use of a continuous process in which small amounts of the lithiated intermediate are continuously produced and reacted with the borate to form the boronic acid product reduces accumulation of the energetic, reactive lithiated intermediate, thus providing a safer process. The use of a continuous process where reduced quantities of the reactants are cooled to temperatures of less than −60° C. at a given time also improves energy efficiency, and reduces equipment size, equipment costs, and overall cycle time. Due to the potential for shorter residence times in continuous processes, it may be possible to operate at higher temperatures, such as temperatures of greater than −60° C., but less than −30° C., without In addition to lowering an overall yield of the process, formation of the reactive substituted benzyne may present safety hazards.

FIG. 1 illustrates a system 100 that may be used in the method of forming the boronic acid. The system 100 may include two reactors (i.e., first reactor 102 and second reactor 104) that may be flowably interconnected by a transfer tube 106. The first reactor 102 may be a container or vessel having an internal volume of between about 200 ml and about 5 ml and, more particularly, about 25 ml. The transfer tube 106 may be a hollow tube having an internal volume of between about 10 ml and about 0.5 ml and, more particularly, about 3 ml. The second reactor 104 may be a container or vessel having an internal volume of between about 300 ml and about 5 ml and, more particularly, about 30 ml.

The first reactor 102 and the second reactor 104 each include ports for reagent addition and product removal. Each of the first reactor 102 and the second reactor 104 may be fitted with a nitrogen tube that is flowably interconnected to a nitrogen bubbler via, for example, a common header leading. Nitrogen flow to the nitrogen bubbler may be adjusted to provide a slight nitrogen pad on the system 100. Agitation to the reactors 102 and 104 is supplied via small stir bars with the entire system 100 apparatus positioned over a multi zone stir plate 128, or via mechanically driven stir shafts positioned through ports in the reactor heads.

Agitation may be initiated in the first reactor 102 and the second reactor 104. The system 100 may be cooled to less than about −50°, or in alternative embodiments, less than about −60° C. by placing the system 100 in a bath 108 containing a mixture of dry ice and a solvent (e.g., acetone, 2-propanol or hexane). Larger vessels could be jacketed and cooled using a cryogenic cooling unit. The bath may be maintained at a temperature sufficient to maintain this temperature, such as less than about −70° C. It has been observed that a different implementation, such as a tube reactor design, might allow a somewhat higher operating temperature due to a shorter residence time.

A solution of the 1-chloro-2-substituted-3-fluorobenzene may be prepared by dissolving the 1-chloro-2-substituted-3-fluorobenzene in a solvent. By way of example and not limitation, the 1-chloro-2-substituted-3-fluorobenzene may include 2,6-CFA. Examples of suitable solvents include, but are not limited to, anhydrous 1,2-dimethoxyethane (DME), diethyl ether, and tetrahydrofuran (THF). The 1-chloro-2-substituted-3-fluorobenzene solution may be loaded into a first pump 110 flowably interconnected to the first reactor 102.

The alkyllithium may be dispersed in an organic solvent, such as a hexane, and may be loaded into a second pump 112 flowably interconnected to the first reactor. For example, the alkyllithium may include a butyllithium (e.g., n-butyllithium), a methyllithium, or a propyllithium.

The borate may be loaded into a third pump 114 flowably interconnected to the second reactor 104. For example, the borate may include trimethyl borate or triisopropyl borate. The 1-chloro-2-substituted-3-fluorobenzene solution may be introduced to the first reactor 102 using the first pump 110, and the alkyllithium may be introduced to the first reactor using the second pump 112. Flow rates of the 1-chloro-2-substituted-3-fluorobenzene solution and the alkyllithium into the first reactor 102 may be determined, for example, based on molar equivalents. For example, the flow rate of the 1-chloro-2-substituted-3-fluorobenzene solution from the first pump 110 may be between about 2 ml/minute and about 0.2 ml/minute and, more particularly, about 0.7 ml/minute. The flow rate of the alkyllithium from the second pump 112 may be between about 0.7 ml/minute and about 0.05 ml/minute and, more particularly, about 0.3 ml/minute. In other particular embodiments, higher flow rates may used.

A first feed line 118 may be used to direct the 1-chloro-2-substituted-3-fluorobenzene solution from the first pump 110 through a reactor head port 116A into the first reactor 112 below a surface of liquid contained therein. A second feed line 120 may be used to direct the alkyllithium from the second pump 112 through the reactor head port 116A into the first reactor 102. The second feed line 120 may terminate over a surface of the liquid contained in the first reactor 102 or may direct the flow below the liquid surface.

As the 1-chloro-2-substituted-3-fluorobenzene solution and the alkyllithium are directed into the first reactor 102, the bath 108 may be maintained at a temperature of about −60° C. for from about 10 minutes to about 1 hour as a reaction mixture forms in the first reactor 102. The reaction mixture may include the 1-chloro-2-substituted-3-fluorobenzene, the alkyllithium, and the lithiated intermediate formed by reacting the 1-chloro-2-substituted-3-fluorobenzene and the alkyllithium. In embodiments in which the 1-chloro-2-substituted-3-fluorobenzene comprises 2,6-CFA and the alkyllithium comprises n-butyllithium, the lithiated intermediate may comprise a Li-2,6-CFA.

As the first reactor 102 fills with a reaction mixture, the reaction mixture may begin to flow from the first reactor 102 through the transfer tube 106 and into the second reactor 104. As the reaction mixture flows through the transfer tube 106 into the second reactor 104, the third pump 114 may be used to introduce the borate to the reaction mixture in the second reactor 104. For example, a flow rate of the borate from the third pump 114 may be between about 1 ml/minute and about 0.01 ml/minute and, more particularly, about 0.08 ml/minute. A third feed line 122 may be used to direct the borate from the third pump 114 through a reactor head port 116B of the second reactor 104. The borate may be dripped from the third feed line 122 to a surface of the liquid contained within the second reactor 104. As the borate is introduced into the second reactor 104, an intermediate solution including the boronate may be formed. In embodiments in which the 1-chloro-2-substituted-3-fluorobenzene comprises 2,6-CFA, the alkyllithium comprises n-butyllithium and the borate comprises methyl borate, the boronate may comprise PBA-diMe.

As the second reactor 104 fills with the intermediate solution, the intermediate solution may be transferred into a flask 124 through an exit tube 126. For example, the intermediate solution may be removed from the second reactor 104 to maintain a volume of about 30 ml of liquid in the second reactor 104. The intermediate solution may be accumulated in the flask 124 at room temperature. For example, the intermediate solution may be removed from the flask every 20 to 30 minutes as the reaction continues to run.

The boronate in the intermediate solution may be converted to the boronic acid by treatment with aqueous potassium hydroxide (KOH) followed by acidification. In embodiments in which the boronate comprises PBA-diMe, the PBA-diMe may be converted to PBA by treatment with aqueous potassium hydroxide followed by acidification.

The following examples serve to explain embodiments of the present disclosure in more detail. These examples are not to be construed as being exhaustive or exclusive as to the scope of this invention.

EXAMPLES

Example 1

Determination of Process Chemistry for Formation of PBA

A freshly prepared solution of Li-2,6-CFA was examined in a differential scanning calorimeter (DSC). Each of the reactants was kept at a temperature of less than −78° C. during sample preparation. The sample was then heated slowly in the DSC and the heat released during the process was monitored.

Figure 2:
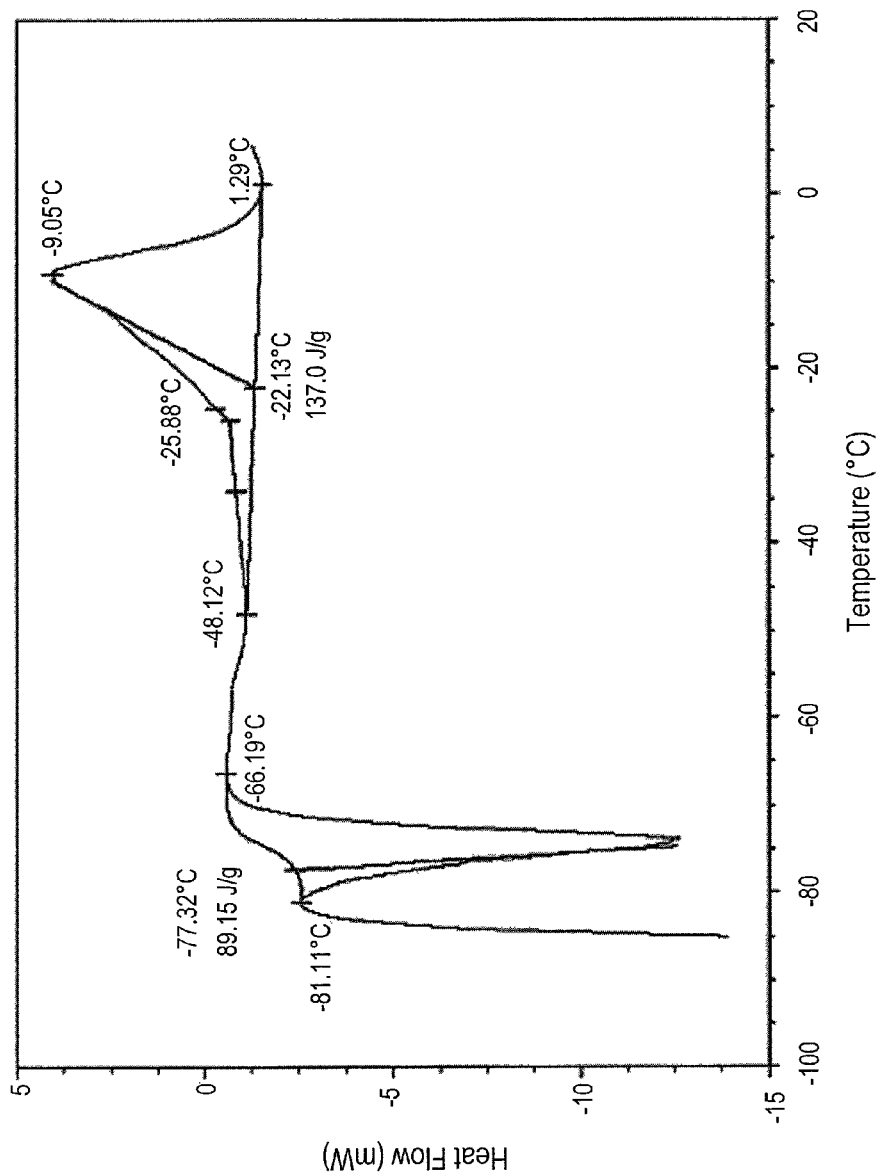
FIG. 2 is a differential scanning calorimeter (DSC) curve of a 6-chloro-2-fluoro-3-litihioanisole solution in nitrogen.

As shown in FIG. 2, a DSC scan of the freshly prepared solution of Li-2,6-CFA in nitrogen was performed. Degradation (side) reactions were first detected in the DSC at about −48° C. In nitrogen, a slow initial phase of the reaction was observed until about −26° C. was reached and then the reaction proceeded rapidly. The peak reaction temperature is at about −9° C. and the reaction is completed at about 1° C. A total exothermic heat of reaction is 137 J/g of solution or 1370 J/g of reactant (226 kJ/mol of Li-2,6-CFA).

When the reaction mixture decomposes, there is a loss of desired product and an increasing coloration of the reaction mixture, from clear and colorless to yellow to dark brown-black. Support for the decomposition pathway by elimination of lithium fluoride is given by the observation of 4,3'-dichloro-2-fluoro-3,2'-dimethoxybiphenyl by GC-MS analysis.

Figure 3:
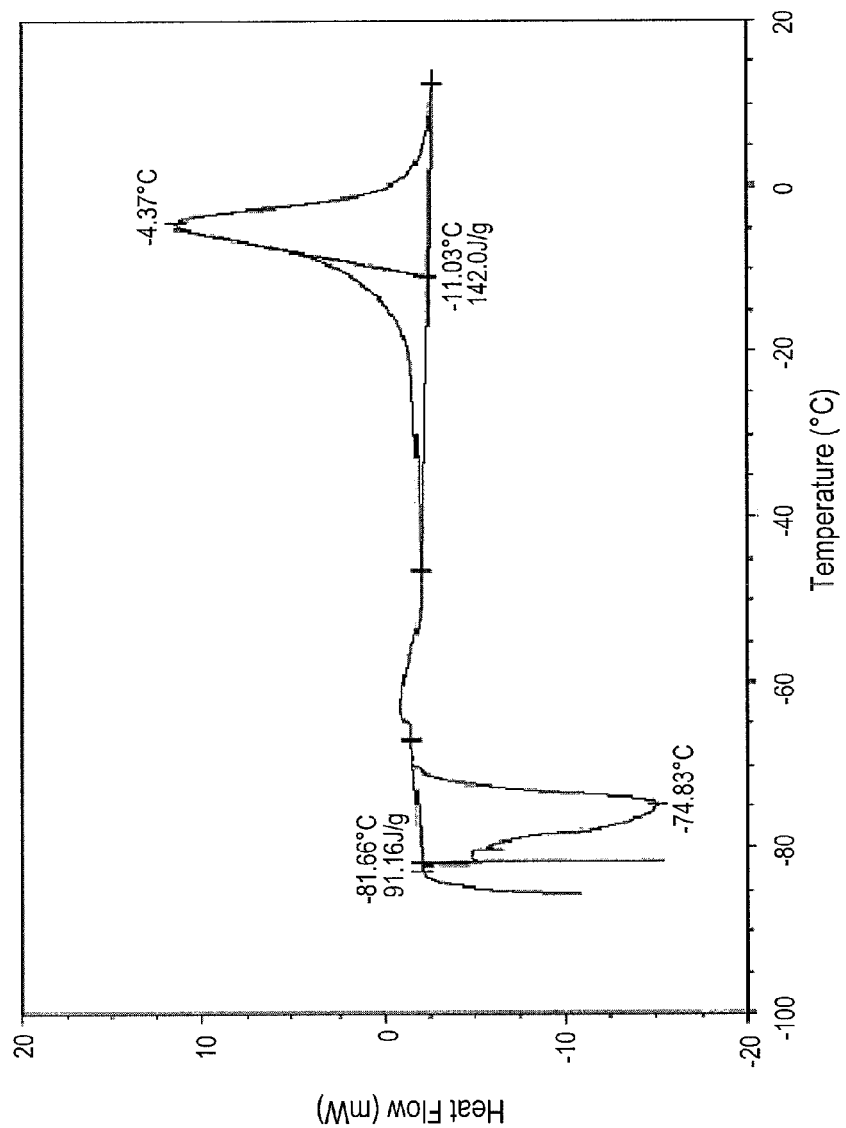
FIG. 3 is a DSC curve of a 6-chloro-2-fluoro-3-litihioanisole solution in ambient air.

As shown in FIG. 3, a DSC scan of the freshly prepared solution of Li-2,6-CFA in ambient air was also performed. The observed onset temperature was the same and the peak temperature shifted to −5° C. The heat of reaction was 142 J/g of solution exothermic (234.3 kJ/mol of 2,6-Li-CFA). It is not known what factors make this reaction more exothermic than the same reaction in nitrogen.

Example 2

Formation of PBA in a Continuous Stirred-Tank Apparatus

The system 100 shown in FIG. 1 was configured with a first reactor 102 having an internal volume of about 25 ml, a transfer tube 106 having an internal volume of about 3 ml and a second reactor 104 having an internal volume of about 30 ml.

Agitation was started in the first reactor 102 and the second reactor 104. The system 100 was cooled to about −60° C. by placing the first reactor 102 and the second reactor 104 in the bath 108 containing dry ice in hexane and maintained at a temperature of about −70° C. A solvent level of the bath 108 was checked to assure that the transfer tube 106 was covered with the solvent.

A solution of 2-chloro-6-fluoroanisole (2,6-CFA) (31.4 g, 190 mmol) in anhydrous 1,2-dimethoxyethane (DME) (241 ml) was prepared in a 500 ml bottle. Molecular sieves were added to remove water, and water content was measured by Karl Fischer titration to assure the 2,6-CFA solution contained less than about 100 ppm water (about 35 ppm measured). The 2,6-CFA solution in the 500 ml bottle was placed on a balance and fitted with a cap holding the inlet tube to metering pump 110. (i.e, first pump 110). A mixture of n-butyllithium in hexanes (2.5 M, 102 ml) was loaded into another (syringe) pump (i.e., second pump 112) and trimethyl borate (25.7 g, 28 ml) was loaded into a syringe and was placed on a separate syringe pump (i.e., third pump 114).

The first, second, and third feed lines 118, 120, 122 were respectively pumped full of the 2,6-CFA, the n-butyllithium and the methyl borate to just short of the tube exit prior to the start of the experiment. When the solvent bath temperature was about −74° C., the first pump 110 containing the 2,6-CFA and the second pump 112 containing the n-butyllithium were started with flow rates of 0.73 ml/min and 0.27 ml/min, respectively. The first feed line 118 was formed from polytetrafluoroethylene (PTFE) tubing and was directed through the reactor head port 116A into the first reactor 102 below the liquid surface. The n-butyllithium addition was added to the first reactor 102 through the second feed line 120 that terminated just above the liquid surface in the first reactor 102.

The solvent bath was monitored and dry ice was added to the solvent bath to maintain the temperature of the system 100 at less than about −60° C. The third feed line 122 for the trimethyl borate was directed into the second reactor 104 to drip above the liquid surface. After about 26 minutes, when the first reactor 102 was full and the reaction mixture was flowing through the transfer tube into the second reactor 104, the third pump 114 was started at a flow rate of the trimethyl borate of about 0.08 ml/min.

After about 37 minutes, as the second reactor 104 filled, flow was started from an exit tube 126 to maintain reaction mixture volume in the second reactor 104 near about 30 ml. Intermediate solution from the second reactor 104 was accumulated in the flask 124 at room temperature. The intermediate solution was weighed and transferred to sample jars every 20 to 30 minutes. The experiment was run for 4 hours. A total of about 153 g of the intermediate solution containing PBA-diMe was collected. A gas chromatography (GC) method with internal standard was used to quantify the amount of PBA-diMe in the intermediate solution. A conversion to PBA-diMe of about 92% was calculated with about 8% of the original unconverted 2,6-CFA also quantified.

The PBA-diMe in the intermediate solution was converted to PBA product by treatment with aqueous potassium hydroxide (KOH) followed by acidification. The intermediate solution was transferred to a 500 ml flask and placed in a cool water bath on a stir plate. A KOH solution was prepared using 22 g of 45% aqueous KOH diluted with 87 ml of deionized water to make 109 g of 9% KOH solution (2 equivalents). With the intermediate solution temperature at about 16° C., the aqueous KOH solution was added dropwise to the intermediate solution with an addition funnel over about 10 minutes. The solution was subsequently mixed for 50 minutes at 20° C. to form a reaction mixture. The reaction mixture was filtered to remove a small amount (less than about 0.2 g) of white solids using a Buchner funnel and a water aspirator. The reaction mixture was then transferred to a separatory funnel and allowed to separate. After 50 minutes the bottom (aqueous) layer was transferred to a 500 ml flask. Sodium chloride (about 3 g) was added and the reaction mixture was extracted with tert-butyl methyl ether (105 ml, 78 g) for about 30 minutes. The reaction mixture was transferred to a separatory funnel. After about 30 minutes the bottom (aqueous) layer was transferred to a flask and 36% hydrochloric acid (HCl) (4 equivalents, 35 g (30 ml) of 36% solution) was added dropwise with an addition funnel. The solution was stirred for about 15 minutes. An amorphous mass of white solid was observed. Acetonitrile (64 g, 81 ml) was added and the solution was stirred for about 20 minutes at about 20° C. The solution was transferred to a separatory funnel and allow to separate for 50 minutes. An upper (organic) product layer was transferred to a sample jar. Analysis of the acetonitrile solution of PBA product showed 13% PBA by weight for a 67% recovery of PBA.

Example 3

Formation of PBA in a Tubular Reactor Apparatus

Figure 4:
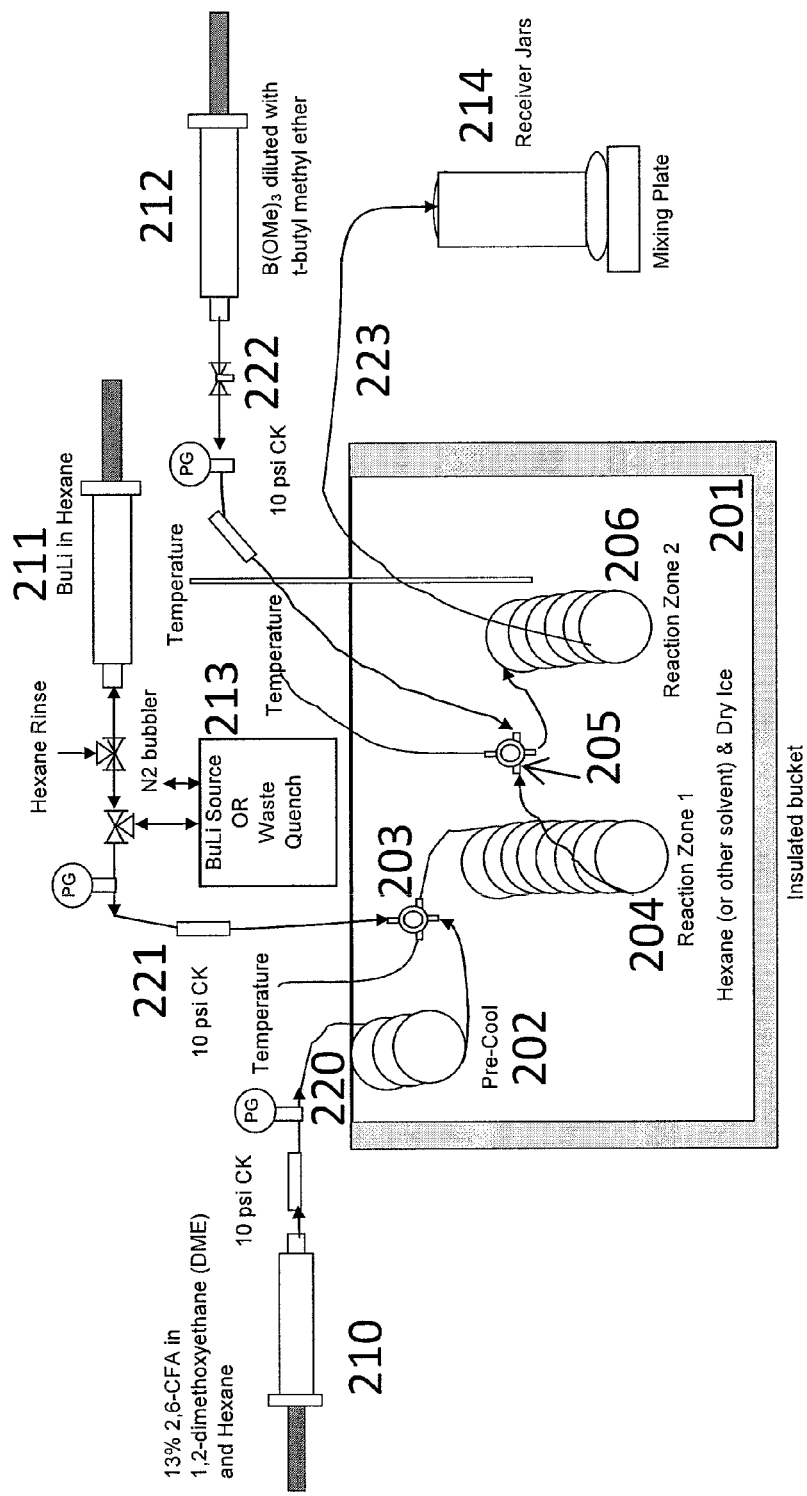
FIG. 4 is a schematic diagram of an embodiment of a system used to form boronic acids using tubular reactors.

The system 200 shown in FIG. 4 was configured with a pre-cooling zone 202 (consisting of 1/8" stainless steel tubing), a first mixing zone 203 (consisting of a 1/4" cross fitting followed by an in-line plastic static mixer), a first reaction zone 204 (consisting of 1/8" stainless steel tubing), a second mixing zone 205 (consisting of a 1/8" cross fitting followed by an in-line plastic static mixer), and a second reaction zone 206 (consisting of 1/8" stainless steel tubing), all submerged in a dry ice/hexane bath 201. The in-line plastic static mixers in mixing zones 203 and 205 had dimensions of 2.25 inch by 3/16 inch and were installed in each segment to force the reaction solution to mix and fold on itself. Check valves were installed in reagent feed lines 220 (consisting 1/8" stainless steel tubing), 221 (consisting of 1/4" Teflon tubing), and 222 (consisting of 1/8" stainless steel tubing) to prevent back-flow of reagents.

Flow of anhydrous 1,2-dimethoxyethane (DME) and anhydrous hexanes was initiated through reagent feed line 220 while dry ice/hexane bath 201 was used to cool the reactor system to the desired −60° C. reaction temperature. Thermocouples were used to monitor fluid temperature at mixing zones 203 and 205.

A feed solution consisting of 13% 2-chloro-6-fluoroanisole (2,6-CFA), 57% DME, and 30% hexane (by weight) was prepared and loaded into the syringe of pump 210. The addition of hexane was necessary to suppress the freezing point of solution and avoid plugging in reagent feed line 220. A feed solution of 2.5M butyllithium in hexanes was loaded into the syringe of pump 211. A feed solution of 30% trimethyl borate and 70% 2-methoxy-2-methylpropane (by weight) was prepared and loaded into the syringe of pump 212. Dilution in 2-methoxy-2-methylpropane (TBME) was necessary to suppress the freezing point of solution and avoid plugging in reagent feed line 222. All reagents and solvents were dried over molecular sieves prior to loading.

Flow of 2,6-CFA (in DME and hexane) was initiated using syringe pump 210. The 2,6-CFA solution was delivered at 0.69 mL/min through reagent feed line 220 and cooled through the pre-cooling loop 202 before reaching mixing zone 203. When the pre-cooling zone 202 was almost full, flow of butyllithium (in hexanes) was started using pump 211. In mixing zone 203, the 2,6-CFA solution was mixed with butyllithium solution that was delivered at 0.31 mL/min through reagent feed line 221. The total flow rate through mixing zone 203 and reaction zone 204 was approximately 1.0 mL/min with a residence time in mixing zone 203 and reaction zone 204 of approximately 7 minutes. In mixing zone 203 and reaction zone 204, the 2,6-CFA and butyllithium reacted to form Li-2,6-CFA.

When reaction zone 204 was almost full, flow of trimethyl borate (in TBME) was initiated using syringe pump 212. The Li-2,6-CFA solution from reaction zone 204 flowed into mixing zone 205, where it was mixed with trimethyl borate solution that was delivered at 0.31 mL/min through reagent feed line 222. The total flow rate through mixing zone 205 and reaction zone 206 was approximately 1.3 mL/min with a residence time in mixing zone 205 and reaction zone 206 of approximately 6 minutes. In mixing zone 205 and reaction zone 206, the Li-2,6-CFA reacted with trimethyl borate to form the PBA-diMe product. The PBA-diMe product flowed through the discharge line 223, where it was collected in receiving jar 214 and subsequently worked up. Analysis of the PBA solution indicated 45% conversion of 2,6-CFA to PBA.

Example 4

Decomposition of Li-2,6-CFA Monitored by In Situ IR Spectroscopy 250 mL Round-Bottom Flask in Cooling Bath The Li,2-6-CFA species was generated to allow for monitoring of its thermal decomposition by in situ IR spectroscopy. DME was loaded into a 250 mL glass round-bottom flask. The flask was lowered into a cooling bath filled with 2-propanol and chilled to approximately −60° C. with a cryogenic finger. Agitation was started. The depth of the flask was adjusted to control the temperature of solution at approximately −50° C. The probe of an in situ IR spectrometer was inserted into the reaction solution through a port in the neck of the flask and data collection was initiated. A background signal for DME at approximately −50° C. was obtained.

2,6-CFA was added to the flask to form a solution of 13% (by weight) 2,6-CFA in DME. The reaction solution was cooled to approximately −58° C. 1.15 molar equivalents of butyllithium (2.5 M in hexanes) were delivered to the flask by syringe above the liquid surface to convert the 2,6-CFA to Li-2,6-CFA. The addition rate was controlled to maintain the temperature of the solution at less than −50° C. The solution was allowed to react for one hour.

Figure 5:
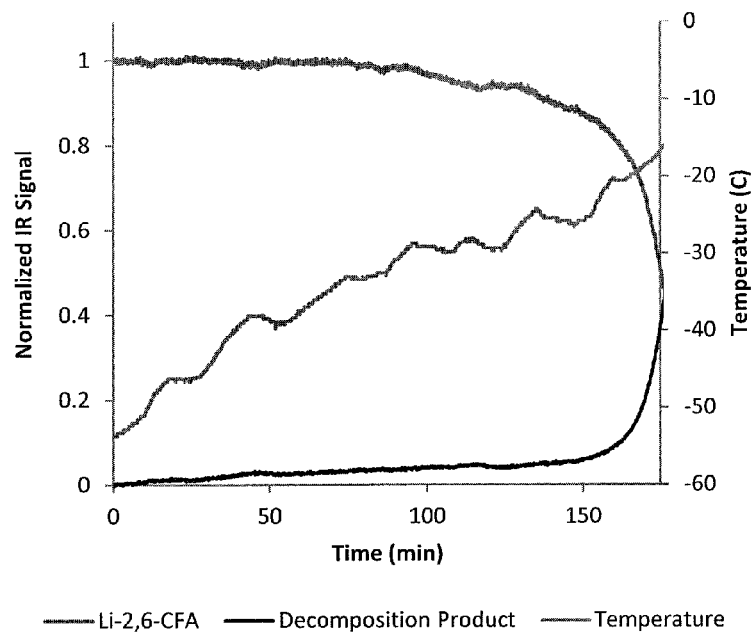
FIG. 5 is a graph of the relative concentration of the Li-2,6-CFA intermediate and its decomposition products with changing temperature, collected with an in situ IR instrument.

Decomposition of Li-2,6-CFA was monitored by in situ IR by slowly increasing the temperature of the reaction solution and observing for changes in IR bands that indicated Li-2,6-CFA disappearance or decomposition product formation. The Li-2,6-CFA solution temperature was raised to approximately −45° C. and held for 10 minutes with no observable decomposition. The temperature was then raised and held at temperatures of approximately −40° C. for 20 minutes, −35° C. for 10 minutes, and −30° C. for 30 minutes, as shown in FIG. 5. Slow decomposition was noted at −30° C.; however, the rate of decomposition notably increased when the temperature of the reaction solution was increased to approximately −25° C. The rate accelerated even further when the temperature of the reaction solution was increased to approximately −20° C., leading to accelerating solution temperature beyond to capability of the bath to maintain temperature.

150 mL Straight-Walled Vessel in Solid-State Cooling Device

The temperature control provided by the cooling bath and round-bottom flask was not precise, as fluctuations of several degrees occurred at each hold point. To gain more resolution above −30° C., the in situ IR investigation was performed in a 150 mL glass straight-walled reactor surrounded by a solid-state cooling device that allowed for precise temperature control and rapid, automated response to changes in heat flow. The lower temperature limit of the device was −40° C.

DME and 2,6-CFA were loaded into the vessel to create an approximately 8% 2,6-CFA solution (by weight). Agitation was started. The reaction solution was cooled to approximately −35° C. The probe of the in situ IR spectrometer was inserted into the reaction solution through a port in the reactor head and IR data collection was started. To generate the Li-2,6-CFA species, 1.15 molar equivalents of butyllithium (2.5 M in hexanes) were delivered to the reaction vessel above the liquid surface via syringe. The solution was allowed to react for approximately 30 minutes at −40° C.

Figure 6:
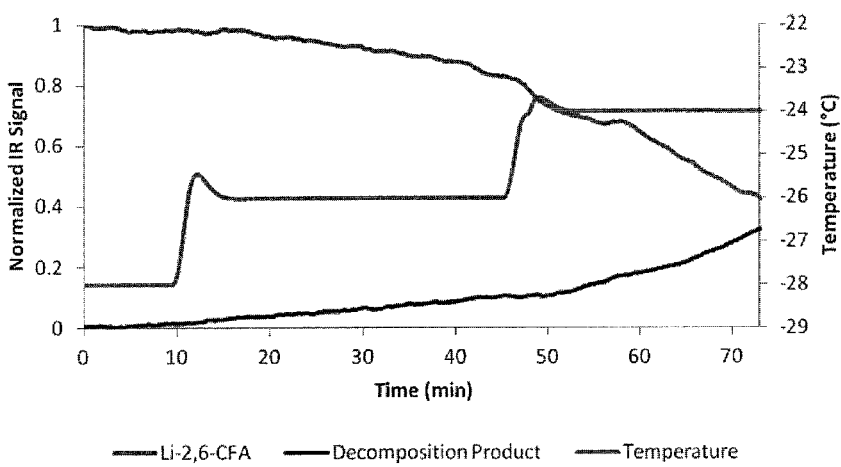
FIG. 6 is a graph of the acceleration of Li-2,6-CFA decomposition above −28° C.

The solution temperature was raised to −28° C. and held with little to no decomposition observed. When the solution temperature was raised to −26° C., the decomposition product IR signal was observed to build in intensity while the Li-2,6-CFA IR signal was observed to decrease, as shown in FIG. 6. Further acceleration in the rate of decomposition was observed when the solution temperature was raised to −24° C. These data provided a detailed view of decomposition behavior with precise temperature control, suggesting Li-2,6-CFA decomposition begins to rapidly accelerate at temperatures in excess of −28° C.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method of forming a 4-choloro-2-fluoro-3-methoxyphynylboronic acid, comprising:
   minimizing decomposition of a 6-chloro-2-fluoro-3-lithioanisole by applying a continuous process of forming a 4-choloro-2-fluoro-3-methoxyphynylboronate, wherein the process comprises:
   (i) continuously adding a 2-chloro-6-fluoroanisole and at least one alkyllithium to a first reactor to form the 6-chloro-2-fluoro-3-lithioanisole, while continuously transferring the formed 6-chloro-2-fluoro-3-lithioanisole from the first reactor into a second reactor; and
   (ii) continuously adding a borate to the second reactor, wherein the borate reacts with the 6-chloro-2-fluoro-3-lithioanisole to form the 4-choloro-2-fluoro-3-methoxyphynylboronate, while continuously transferring the formed 4-choloro-2-fluoro-3-methoxyphynylboronate from the second reactor into a receiving container to maintain a reaction mixture volume within the second reactor,
   wherein the first and the second reactors are maintained at a temperature of less than about −50° C.; and
   converting the 4-choloro-2-fluoro-3-methoxyphynylboronate to the 4-choloro-2-fluoro-3-methoxyphynylboronic acid.

2. The method of claim 1, wherein continuously adding a 2-chloro-6-fluoroanisole and at least one alkyllithium to a first reactor comprises continuously adding the 2-chloro-6-fluoroanisole and at least one of a butyllithium, a methyllithium, and a propyllithium to the first reactor.

3. The method of claim 1, wherein continuously adding a 2-chloro-6-fluoroanisole and at least one alkyllithium to a first reactor comprises continuously adding the 2-chloro-6-fluoroanisole and at least one of n-butyllithium, t-butyllithium, and sec-butyllithium to the first reactor.

4. The method of claim 1, wherein continuously adding a borate to the second reactor comprises continuously adding trimethyl borate to the second reactor.

5. The method of claim 1, wherein converting the 4-choloro-2-fluoro-3-methoxyphynyl boronate to the 4-choloro-2-fluoro-3-methoxyphynylboronic acid comprises:
   exposing the 4-choloro-2-fluoro-3-methoxyphynylboronate to aqueous potassium hydroxide; and
   performing an acidification process.

6. The method of claim 1, wherein continuously adding a borate to the second reactor comprises continuously adding at least one of trimethyl borate and triisopropyl borate to the second reactor.

7. A method of continuously forming a 4-choloro-2-fluoro-3-methoxyphynylboronate while minimizing decomposition of a 6-chloro-2-fluoro-3-lithioanisole intermediate compound, the method comprising:
   continuously adding a 2-chloro-6-fluoroanisole and at least one alkyllithium to a first reactor to form the 6-chloro-2-fluoro-3-lithioanisole, while the formed 6-chloro-2-fluoro-3-lithioanisole continuously leaves the first reactor and enters a second reactor; and
   continuously adding a borate to the second reactor, wherein the borate reacts with the 6-chloro-2-fluoro-3-lithioanisole in the second reactor to form the 4-choloro-2-fluoro-3-methoxyphynylboronate, while the formed 4-choloro-2-fluoro-3-methoxyphynylboronate continuously leaves the second reactor and enters into a receiving container.

8. The method of claim 7, wherein the first and the second reactors are maintained at a temperature of less than about −30° C.

9. The method of claim 7, wherein the first and the second reactors are maintained at a temperature of less than about −50° C.

10. The method of claim 7, wherein the first and the second reactors are maintained at a temperature of less than about −60° C.

11. A continuous tubular process of forming a 4-choloro-2-fluoro-3-methoxyphynylboronate, the process comprising:
    continuously feeding a starting material mixture comprising a 2-chloro-6-fluoroanisole and an alkyllithium into a first reaction zone of a tubular reactor apparatus to form a reaction mixture comprising an 6-chloro-2-fluoro-3-lithioanisole intermediate, while continuously withdrawing the formed reaction mixture comprising the 6-chloro-2-fluoro-3-lithioanisole intermediate from the first reaction zone into a second reaction zone of the tubular reactor; and
    continuously feeding a borate to the reaction mixture in the second reaction zone to form the 4-choloro-2-fluoro-3-methoxyphynylboronateboronate, while continuously withdrawing the 4-choloro-2-fluoro-3-methoxyphynylboronateboronate from the second reaction zone of the tubular reactor apparatus into a receiving container.

12. The method of claim 11, wherein the tubular reactor apparatus is maintained at a temperature of less than about −30° C.

13. The method of claim 11, wherein the tubular reactor apparatus is maintained at a temperature of less than about −40° C.

14. The method of claim 11, wherein the tubular reactor apparatus is maintained at a temperature of less than about −50° C.

15. The method of claim 11, wherein the first and the second zone of the tubular reactor apparatus comprise stainless steel tubing.

16. The method of claim 7, wherein continuously adding a 2-chloro-6-fluoroanisole to a first reactor comprises continuously adding the 2-chloro-6-fluoroanisole to the first reactor below a surface of liquid contained in the first reactor.

17. The method of claim 7, wherein continuously adding at least one alkyllithium to a first reactor comprises continuously adding the at least one alkyllithium to the first reactor over a surface of liquid contained in the first reactor.

18. The method of claim 7, wherein continuously adding at least one alkyllithium to a first reactor comprises continuously adding the at least one alkyllithium to the first reactor below a surface of liquid contained in the first reactor.

19. The method of claim 7, wherein the receiving container is at room temperature.

20. The method of claim 7, further comprising converting the 4-choloro-2-fluoro-3-methoxyphynylboronate collected in the receiving container to a 4-choloro-2-fluoro-3-methoxyphynylboronic acid.

21. The method of claim 20, wherein converting the 4-choloro-2-fluoro-3-methoxyphynylboronate collected in the receiving container to a 4-choloro-2-fluoro-3-methoxyphynylboronic acid comprises:
    transferring at least a portion of the 4-choloro-2-fluoro-3-methoxyphynylboronate in the receiving container to a reaction container;
    reacting the 4-choloro-2-fluoro-3-methoxyphynylboronate in the reactor container with an aqueous potassium hydroxide, followed by performing an acidification process to provide the 4-choloro-2-fluoro-3-methoxyphynylboronic acid.

22. The method of claim 11, further comprising:
cooling the 2-chloro-6-fluoroanisole in a pre-cooling zone of the tubular reactor apparatus prior to mixing the 2-chloro-6-fluoroanisole with the alkyllithium to provide the starting material mixture.

23. The method of claim 11, further comprising:
mixing the 2-chloro-6-fluoroanisole and the alkyllithium in a first mixing zone of the tubular reactor apparatus to provide the starting material mixture that is subsequently continuously fed into the first reaction zone of the tubular reactor apparatus.

24. The method of claim 11, further comprising converting the 4-choloro-2-fluoro-3-methoxyphynylboronate collected in the receiving container to a 4-choloro-2-fluoro-3-methoxyphynylboronic acid.

25. The method of claim 24, wherein converting the 4-choloro-2-fluoro-3-methoxyphynylboronate collected in the receiving container to a 4-choloro-2-fluoro-3-methoxyphynylboronic acid comprises:
transferring at least a portion of the 4-choloro-2-fluoro-3-methoxyphynylboronate in the receiving container to a reaction container;
reacting the 4-choloro-2-fluoro-3-methoxyphynylboronate in the reactor container with an aqueous potassium hydroxide, followed by performing an acidification process to provide the 4-choloro-2-fluoro-3-methoxyphynylboronic acid.

* * * * *